(12) United States Patent
Powell et al.

(10) Patent No.: US 9,745,633 B2
(45) Date of Patent: Aug. 29, 2017

(54) DETECTION OF PNA CLAMPING

(71) Applicants: Michael J Powell, Alamo, CA (US);
Aiguo Zhang, San Ramon, CA (US)

(72) Inventors: Michael J Powell, Alamo, CA (US);
Aiguo Zhang, San Ramon, CA (US)

(73) Assignee: DIACARTA LTD, George Town (KY)

( * ) Notice: Subject to any disclaimer, the term of this patent is extended or adjusted under 35 U.S.C. 154(b) by 357 days.

(21) Appl. No.: 14/472,240

(22) Filed: Aug. 28, 2014

(65) Prior Publication Data

US 2015/0176065 A1     Jun. 25, 2015

Related U.S. Application Data

(60) Provisional application No. 61/840,943, filed on Jun. 28, 2013.

(51) Int. Cl.
*C12Q 1/68*     (2006.01)

(52) U.S. Cl.
CPC ......... *C12Q 1/6886* (2013.01); *C12Q 1/6858* (2013.01); *C12Q 2600/156* (2013.01)

(58) Field of Classification Search
None
See application file for complete search history.

(56) References Cited

U.S. PATENT DOCUMENTS

| 5,635,352 | A | * | 6/1997 | Urdea | C12Q 1/6813 |
| | | | | | 435/6.1 |
| 5,989,813 | A | * | 11/1999 | Gerdes | C07H 21/00 |
| | | | | | 435/6.11 |
| 2007/0039866 | A1 | * | 2/2007 | Schroeder | G01N 27/44769 |
| | | | | | 210/265 |
| 2008/0220428 | A1 | * | 9/2008 | Aichinger | C12Q 1/689 |
| | | | | | 435/6.15 |

FOREIGN PATENT DOCUMENTS

GB     EP 0416817 B1 * 10/1996 ............. C07H 21/00

OTHER PUBLICATIONS

Taback et al. Peptide nucleic acid clamp PCR: a novel K-ras mutation detection assay for colorectal cancer metastases in lymph nodes. Int. J. Cancer 111:409-414 (2004).*
Loupakis et al. KRAS codon 61, 146 and BRAF mutations predict resistance to cetuximab plus irinotecan in KRAS codon 12 and 13 wild-type metastatic colorectal cancer. British Journal of Cancer 101:715-721 (2009).*
Flagella et al. A multiplex branched DNA assay for parallel quantitative gene expression profiling. Analytical Biochemistry 352:50-60 (2006).*

(Continued)

*Primary Examiner* — Samuel Woolwine
(74) *Attorney, Agent, or Firm* — Isaac A. Angres

(57) ABSTRACT

This invention provides methods and systems for detecting sequence variants in a sample nucleic acid. Methods include PNA clamping/PCR using primers with binding moieties followed by capture and detection of amplicons on a solid support. Systems include PCR reagents with primers having binding moieties, a PNA clamping probe, a solid support capable of capturing the PCR amplicons incorporating the binding moieties, and a detector device.

16 Claims, 5 Drawing Sheets

(56) References Cited

OTHER PUBLICATIONS

Newton et al. The production of PCR products with 5' single-stranded tails using primers that incorporate novel phosphoramidite intermediates. Nucleic Acids Research 21(5):1155-1162 (1993).*
Gade et al. Incorporation of nonbase residues into synthetic oligonucleotides and their use in the PCR. GATA 10(2):61-65 (1993).*
Prix et al. Diagnostic biochip array for fast and sensitive detection of K-ras mutations in stool. Clinical Chemistry 48(3):428-435 (2002).*
Thiede et al. Simple and sensitive detection of mutations in the ras proto-oncogenes using PNA-mediated PCR clamping. Nucleic Acids Research 24(5):983-984 (1996).*

* cited by examiner

DETECTION OF PNA CLAMPING

This application claims the priority benefit under 35 U.S.C. section 119 of U.S. Provisional Patent Application No. 61/840,943 entitled "Detection Of PNA Clamping" filed on Jun. 28, 2013, and which is in its entirety herein incorporated by reference.

FIELD OF THE INVENTION

The present inventions relate to methods and systems for sensitive and accurate detection of minor variants to nucleic acid sequences of interest. In particular, methods are directed to the field of detection of minor or single base mutants using PNA clamping techniques in combination with affinity detection techniques on solid support surfaces. Systems are directed to PCR/PNA clamping constituents interacting with affinity detection systems on solid supports.

BACKGROUND OF THE INVENTION

Polymerase chain reaction (PCR) technology can be used to detect the presence of small amounts of particular target polynucleotide sequences through the well known cyclic amplification scheme. The initial quantity of the target nucleic acid can be determined by detecting the amount of amplification product (amplicons) after a certain number of amplification cycles, or using real time PCR techniques that monitor signals from amplicons as they are generated. However, the linearity of PCR amplifications becomes poor with extended cycles. Further, typical real time PCR assays are based on the quantification cycle (CQ) the fractional cycle number where fluorescence increases above the threshold, inherently limited by high background and large increments between reportable values.

For example, real time PCR can be carried out as follows. The process starts with provision of PCR reaction constituents, e.g., at least one pair of specific primers, deoxyribonucleotides, a suitable buffer solution, and a thermo stable DNA polymerase are added to a sample expected to contain a target polynucleotide of interest. If the target sequence is present, anti-sense copies of the sequence between the primer pair will be synthesized by the polymerase enzymes. The product can be melted and the synthesis repeated to make copies of the newly synthesized anti-sense nucleic acids. Further repetitions of polymerization and melting can geometrically expand the number of copies from the original target polynucleotide. A substance marked with a fluorophore can be added to the PCR reaction mixture in a thermal cycler that contains sensors for measuring the fluorescence of the fluorophore after it has been excited at the required wavelength allowing the generation rate of new target polynucleotide copies to be detected as ever increasing fluorescent signals. See, e.g., Dual Resonance Energy Transfer Nucleic Acid Probes, U.S. Pat. No. 7,081,336, by Bao, et al. These measurements can be made after each amplification cycle to generate a trend chart with parameters roughly related (e.g., by a factor of 2, at best) to the initial target sequence quantity. Even these poor results require initial extraction of nucleic acids before analysis can begin.

Because the primer probes can hybridize to imperfect targets, the standard PCR and quantitative PCR methods can have problems accurately detecting target sequences with only minor variants. One way this problem has been addressed is by using peptide nucleic acid (PNA) clamping probe schemes. For example, in Methods and Kits for the Detection of Nucleotide Mutations Using Peptide Nucleic Acid as Both PCR Clamp and Sensor Probe, U.S. Pat. No. 7,803,543, by Chiou, et al., PNA clamping probes to wild type target block amplification of the target nucleic acid unless there is a mutation in the PNA probe footprint. In Chiou, confirmation of sequence variants depends on comparison of PNA and PCR product melting temperatures. However, this and related techniques suffer from ungainly detection procedures, and are not well adapted to precise and accurate quantitative measurements.

There remains a need for sensitive and quantitative methods to detect target nucleic acids in samples. Significant benefits would be provided by solutions to the problem of detecting single base mutations in target nucleic acid sequences of interest. It would be a substantial advancement if rare DNA sequence quantitation could be practiced on crude lysate samples. The present invention provides these and other features, which will be apparent upon complete review of the following.

SUMMARY OF THE INVENTION

The present systems and methods employ complementary aspects of PCR/PNA amplifications and solid support detections to provide highly sensitive and/or quantitatively accurate detection of even minor nucleic acid sequence variants. The present methods also allow sensitive and accurate quantitation of rare sequences from crude samples.

In the general inventive methods, PCR amplification of a target sequence of interest is enhanced by a PNA clamping probe interrogation. The PCR probes are labeled with a binding moiety and/or reporter group, which are ultimately incorporated into resultant PCR amplicon products. To remove background, further enhance sensitivity, and generate a more accurate quantitative signal, the amplicons having binding moieties are captured on a solid support for detection and quantitation.

In one embodiment, the method of detecting a variant in a target nucleic acid of interest includes providing a PCR reaction with a pair of PCR primer probes allowing formation of a PCR process product having a sequence covering a region of interest in the target nucleic acid. At least one of the primer probes has a binding moiety. The reaction also has a PNA clamping probe fully complementary to a clamping target sequence in the nucleic acid target region of interest. The primer probes and clamping probe are mixed with a putative target nucleic acid sample and a PCR amplification process is carried out. The hybridization conditions of PCR reaction stringency and temperature are configured so that the clamping probe hybridizes to a perfect complement clamping target sequence, but fails to hybridize where there are one or more sequence variants in the clamping target sequence. In this way, PCR amplicons are produced, extended from the primer probes, only if extension is not blocked (clamped) by a hybridized PNA probe. That is, if there is a target variant causing a base-pair mismatch between the PNA probe and the target, the PNA probe does not bind to block the PCR extension. Signal from accumulated amplicons confirms there was a variant at the PNA binding site.

Signal from accumulated amplicons can be uniquely confirmed taking advantage of the previous incorporation of one or more binding moieties into the PCR primer probes that were ultimately incorporated into the amplicon product. The methods further include providing a solid support with one or more capture moieties adapted to capture the particular binding moiety elected for incorporation into the primers. Any PCR amplicons present in the reaction solution can be captured on contact with the solid support. After washing the solid support, the capture surface can be interrogated to detect the presence of bound amplicons. An appropriate signal from the capture surface can confirm the presence of a variant in the target sequence. The amplitude of the signal can be interpreted to accurately determine the quantity of variant sequence initially present on the target sequence of interest for the particular sample.

In certain embodiments of the methods, the binding moiety or capture moiety incorporated into the primer can include a member of a useful affinity binding pair. For example, the moiety can include a member having adequate affinity and specificity to function in capture and/or detection procedures in the methods. The methods can employ appropriate ligand/receptor combinations, e.g., binding constituents such as biotin, avidin, streptavidin, a hapten, an antibody, digoxigenin, a polynucleotide comprising a sequence complementary to a capture probe, and a polynucleotide comprising a sequence complementary to a bDNA detection complex.

The nucleic acid target of interest can be any useful target, particularly where there may be substantial significance to the presence of a sequence variant. For example, the nucleic acid target region of interest can be present in an oncogene, a proto-oncogene, an oncogene mutant, a tumor suppressor, a growth factor receptor, a tumor associated signal transduction protein kinase sequence, a K-Ras sequence, a BRCA sequence, a B-Raf sequence, an EGFR sequence, a p53 sequence, a PI3KCA sequence, an IDH1 sequence, a JAK2 sequence, a PTEN sequence, an INK sequence, a pRb sequence, an ARF sequence, a mTOR sequence, an ALK sequence, an Akt sequence, mutants thereof, and/or the like. Further, the target of interest can be any sequence variant, point mutation, translocation or gene deletion in a target gene that encodes a protein that leads to expression of an aberrant cellular activity that leads to a deleterious biological or physiological effect, e.g., such as the development of cancer, metabolic, cardiovascular, inflammatory, neurological disorders, or that leads to the development of resistance to a specific therapeutic modality.

In the clamping step of the method, the PNA clamping probe, and the corresponding nucleic acid target region, have a sequence ranging from, e.g., 6 bases to 35 bases, 8 bases to 30 bases, 15 bases to 25 bases, or about 17 bases. Typically the clamping probe sequence is complementary to a normal or "wild type" sequence. In many cases, a nucleic acid target variant sequence of interest can be a single base pair mismatch, a 2 base mismatch or more in the PNA target region. In many cases, the PNA clamping probe is designed (e.g., by probe length, and base selection) to have a melting point wherein hybridization does not occur with a single base target sequence mismatch at the PCR cycle primer annealing temperature. PNA probes are more sensitive to such mismatches that DNA based probes.

The capture step can take place on a solid support surface. There are many useful solid support substrates known in the art, which can be adapted to function in the present methods. For example, the solid support can be wafers, beads, multiwell plates, microparticles, microplates, and/or the like. The surfaces can be open to optical analysis, or optionally associated with electronic (e.g., capacitance or resonance) sensors. The solid supports are typically insoluble in the contacting solutions, e.g., fabricated from glass, silicon, silica, quartz, plastic, polystyrene, nylon, a semiconductor, a metal, a ceramic, or nitrocellulose. The solid support may include an array of capture elements.

In certain embodiments, the amplicon product of the PNA clamping/PCR process is detected using a bDNA technology. For example, the PCR primer probes can include a capture target sequence and a label target sequence. The PCR product can contact a solid support presenting capture probes or capture extenders with sequences complementary to a unique capture sequence of the amplicon, e.g., a 5' sequence contributed by a primer probe. The amplicon can be captured on the solid support by the first primer probe capture sequence and the second strand of the amplicon can present a sequence complementary to a label extender or amplification multimer sequence of a bDNA detection complex. In this way, the captured amplicon can hybridize to the bDNA label system for detection.

The present inventions include systems for practicing the present methods. For example, the systems can include reagents and hardware to practice the PNA clamping/PCR process. The systems can include solid support detection systems. For example, the detection systems can include solid support surfaces presenting affinity (capture) moieties configured to capture amplicons, and include detection systems configured to detect the appropriate reporter group of the elected label system.

In one embodiment, the system for detecting a variant in a target nucleic acid of interest can include a PCR reaction solution, an amplicon capture solid support, and a detector system configured to interrogate the solid support. For example, the system can include PCR amplification process reaction solution comprising a pair (forward and reverse) of PCR primer probes bracketing a target sequence of interest for amplification. At least one of the primer probes has an incorporated binding moiety. The PCR solution also includes a PNA clamping probe fully complementary to a clamping target sequence in the nucleic acid target region of interest. The system for detecting a variant also includes a solid support comprising a surface with one or more capture moieties adapted to bind the binding moiety of the primer probe and resultant amplicons. The system can include a detector adapted to detect one or more of the pair of primer probes (extended as amplicon constituents) on the solid support.

As described above in the context of variant detection methods, the system components can have certain complementary features in a combination providing sensitive and accurate detection of variants. The primer probes can include a binding target with an affinity for a label system. The PNA clamping probe can be adapted to have a melting temperature less than the primer probe melting temperatures when the clamping target has a sequence variant. The solid support can be a bead, microparticle, a semiconductor, a microplate, or the like. The amplicon detection can be direct by fluorometry or by bDNA methods, e.g., with capture probes or capture extenders associated with the solid support, detection using label extenders, amplification multimers, and/or label probes.

Definitions

Before describing the present invention in detail, it is to be understood that this invention is not limited to particular devices or systems, which can of course vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface"

includes a combination of two or more surfaces; reference to "lysate" includes mixtures of lysates, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

As used herein, the term "lysate" refers to the material resulting from lysis of a cell or tissue. A lysate can be the solution or suspension remaining after cell solids have been removed, e.g., by phase separation, centrifugation, and/or filtration.

As used herein, the term "extracted" refers to being separated from a starting material. For example, nucleic acids are considered extracted from a lysate if most of the non-nucleic acid constituents of the lysate, other than water (e.g., total solids), are separated from the nucleic acids.

An "amplicon", as used herein, is the nucleic acid product of a PCR reaction. Typically, an amplicon includes forward and reverse polymerase products of the PCR amplification, including forward and reverse primers and their extensions.

A "sequence variant" is a sequence that varies in base sequence at one or more nucleotide base positions of a nucleic acid as compared to the sequence of an identified nucleic acid at corresponding positions. For example, given a standard nucleic acid with a sequence of interest fully complementary to a 20 base pair PNA probe, a test nucleic acid has a sequence variant if any one of the nucleotide bases at the corresponding position is not fully complementary to the PNA probe. That is, the test nucleic acid has a sequence variation in the PNA target region, as shown by at least one base pair mis-match between the PNA probe and test nucleic acid in the target region.

A "binding moiety", as used herein, is a group on a PCR primer or PCR amplicon that has an affinity for a particular target group, such as, e.g., a capture moiety on a solid support. For example, given an amplicon with an attached biotin group, and an avidin on a solid support, the biotin would be considered to be the binding moiety.

A "capture moiety" as used herein, is a group on solid support that has an affinity for a particular binding moiety. For example, given an amplicon with an attached target nucleic acid sequence, and a complementary nucleic acid capture sequence on a solid support, the capture sequence would be considered to be the capture moiety.

A "reporter binding moiety" of the present methods and systems is a group on an amplicon or primer having an affinity for a reporter construct and configured to bind the reporter to the amplicon. For example, a hapten on an amplicon or PCR primer is considered a reporter binding moiety in relation to an antibody to the hapten, wherein the antibody is linked, e.g., to a fluorophore reporter.

A "clamping target sequence" is a sequence complementary to a PNA clamping probe sequence. A variant target sequence is a sequence at the PNA target position along a nucleic acid of interest, e.g., but with one or more base mismatches. Often a wild type or normal sequence represents the target sequence and a mutant is considered the variant of the target sequence.

A sequence complementary to another sequence is as known in the art. Nucleic acids with complementary sequences can align 5'-3' to 3'-5' to provide matched base pair sequences. For example, the sequence atgcatgc is complementary to gcatgcat.

The "Tm" (melting temperature) of a nucleic acid duplex under specified conditions (e.g., relevant assay conditions) is the temperature at which half of the base pairs in a population of the duplex are disassociated and half are associated. The Tm for a particular duplex can be calculated and/or measured, e.g., by obtaining a thermal denaturation curve for the duplex (where the Tm is the temperature corresponding to the midpoint in the observed transition from double-stranded to single-stranded form).

Nucleic acids "hybridize" when they specifically associate in solution appropriate conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, New York), as well as Ausubel et al., eds., *Current Protocols*, a joint venture between Greene Publishing Associates, Inc. and John Wiley & Sons, Inc., (supplemented through 2003). Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

Methods of the invention can be optimized for hybridization and washing stringency through empirical studies, or through calculations of preferred conditions. Stringent hybridization conditions are typically at a temperature near the melting temperature ($T_m$) of the complimentary sequences involved. For example, in the context of the present invention, stringent conditions for a given solution are 10° C. or less below the $T_m$, 5° C. or less below the $T_m$, 3° C. or less below the $T_m$, 1° C. below the $T_m$, or at about the $T_m$ of the subject hybridized compliments. The $T_m$ of a DNA-DNA duplex can be estimated using the following equation:

$$T_m(°\text{ C.})=81.5°\text{ C.}+16.6(\log_{10} M)+0.41(\% \ G+C)-0.72(\% \ f)-500/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. See, Rapley and Walker, supra. The $T_m$ of an RNA-DNA duplex can be estimated as follows:

$$T_m(°\text{ C.})=79.8°\text{ C.}+18.5(\log_{10} M)+0.58(\% \ G+C)-11.8(\% \ G+C)^2-0.56(\% \ f)-820/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id. Equations 1 and 2 are typically accurate only for hybrid duplexes longer than about 100-200 nucleotides. Id. The Tm of nucleic acid sequences shorter than 50 nucleotides can be calculated as follows:

$$T_m(°\text{ C.})=4(G+C)+2(A+T),$$

where A (adenine), C, T (thymine), and G are the numbers of the corresponding nucleotides.

DETAILED DESCRIPTION

Methods and systems of the invention employ a combination of features that work together to provide extremely sensitive detection of single base sequence variants, e.g., in complex samples containing very low copy numbers of a nucleic acid of interest. The methods include, e.g., priming a region of interest with PCR probes incorporating binding moieties, blocking PCR amplification of non-variant sequences using a PNA clamping probe, PCR amplification of any target not blocked by the clamping probe to create amplicons, contact and capture of amplicons on a solid support, and detection of the amplicons on the solid support. Systems for practicing the methods include components interacting to amplify and detect variant sequences. For example, systems include PCR reagents, a clamping probe, an amplicon capture surface, and a detector adapted to detect amplicons captured on the surface.

Methods of Detecting Sequence Variants

The methods of detecting variants using PNA clamping probes and solid support detection generally include the steps of combining a sample of interest with PCR primer probes and a clamping probe, completing cycles of the PCR process, contacting the PCR product with specific capture moieties on a solid support, and detecting any amplicons captured on the solid support through binding moieties on the primer probes.

PNA Clamping/PCR Amplification

Peptide nucleic acid (PNA) clamping can be used to detect sequence variants by blocking amplification of more common wild-type sequences. This is accomplished by the PNA probe tightly hybridizing to the wild-type sequence and not allowing read through by a polymerase. PNA is a DNA analogue with nucleobases are linked by peptide bonds, not by phosphate bonds (see, e.g., Nielsen et al., Science 254: 1497-1500, 1991). PNA is not naturally occurring but artificially synthesized. PNAs can include the same four nucleobases as natural DNA. PNA can hybridize quite stringently with a natural nucleic acid having a complementary base sequence. Further, PNA/DNA double strands are destabilized at a larger extent from a single nucleotide mismatch than natural nucleic acids double strands of the same sequences. A common peptide backbone for PNAs is a repeating N-(2-aminoethyl)glycine units linked by amide bonds, providing an electrically neutral backbone.

Figure 1A:
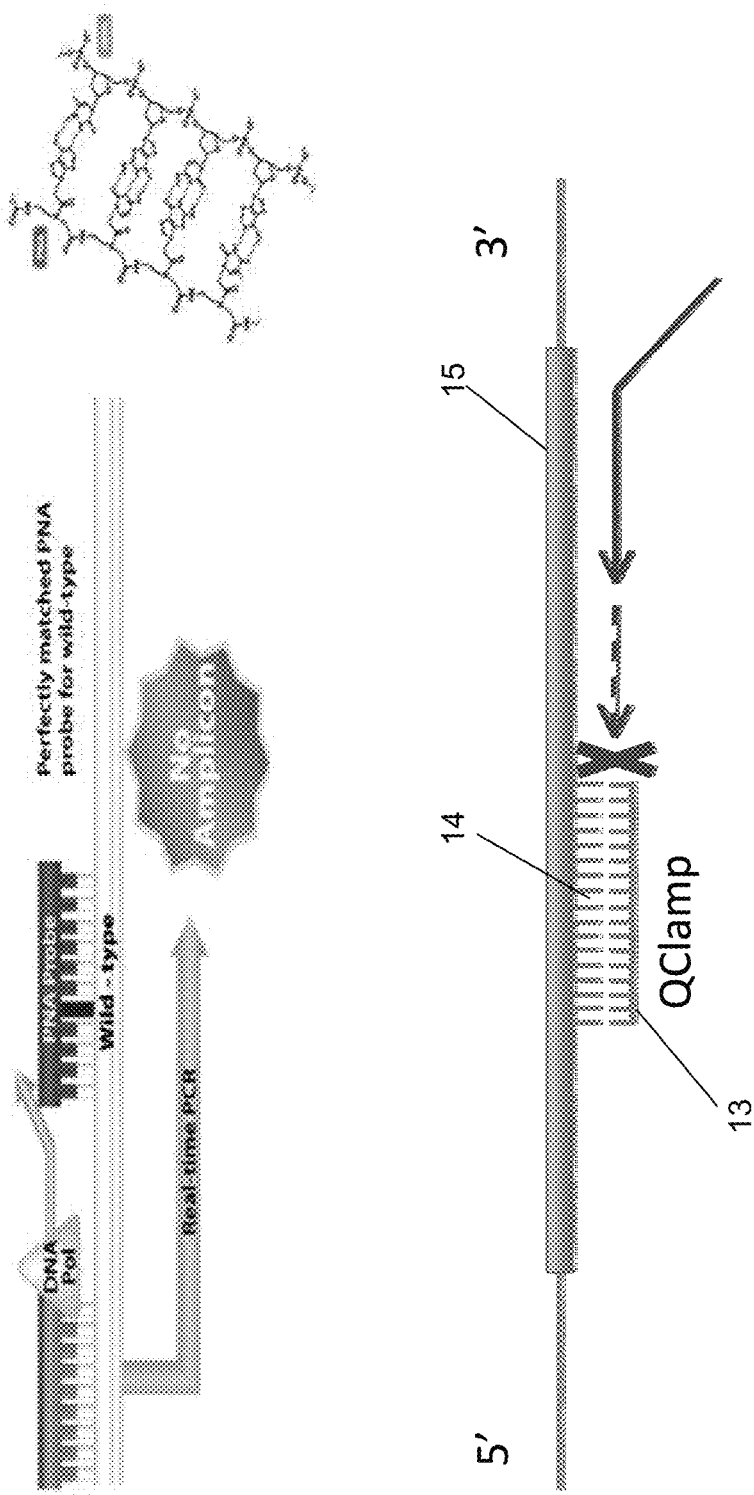
FIG. 1A is a schematic diagram showing a PNA clamping/PCR process wherein the PNA clamping probe blocks extension through a fully matching target sequence.
Figure 1B:
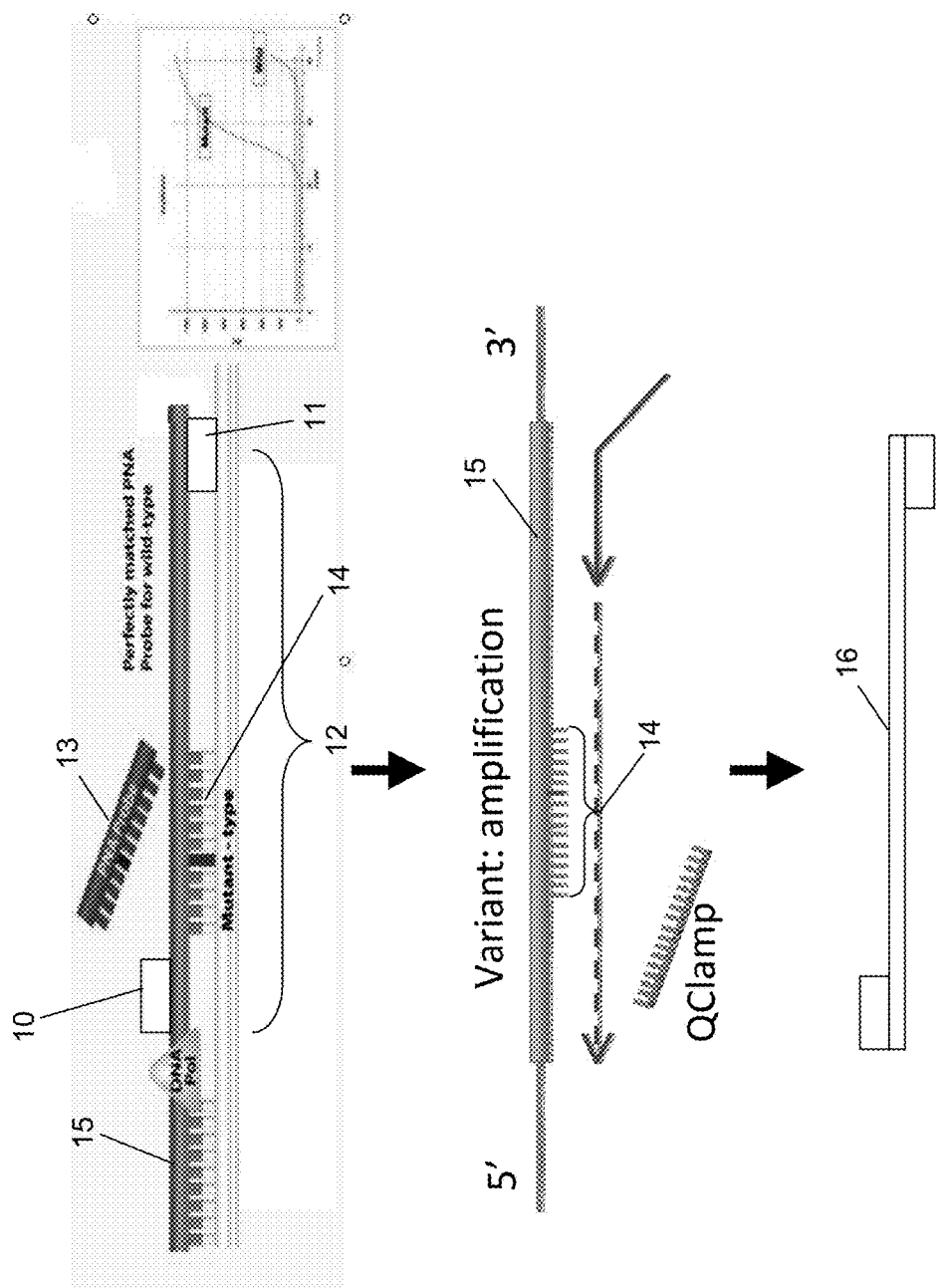
FIG. 1B is a schematic diagram showing a PNA clamping/PCR process wherein PCR extension is not blocked due to a mismatch between the PNA clamping probe and target sequence.

As shown in FIGS. 1A and 1B, PNA clamping/PCR can be carried out by PCR in the presence of a PNA clamping probe. PCR primer probes are prepared forward 10 (e.g., on the coding strand) and reverse 11 bracketing a region of interest 12 in a target nucleic acid. A PNA clamping probe 13 is prepared with a sequence complementary to a clamping target sequence 14. The primer probes and clamping probe are mixed in a PCR reaction solution along with a sample nucleic acid 15 putatively including the target sequence or a variant. In the presence of a polymerase and appropriate nucleotide triphosphates antisense copies of sequences are extended from the PCR primers. If the PNA clamping probe has bound, e.g., to its perfect compliment, it will block extension and rounds of amplification can not take place (FIG. 1A). If there are, e.g., one or more sequence variants in the PNA clamping target, no blocking will occur and amplicons 16, incorporating the primers, will accumulate with every round of PCR amplification (FIG. 1B). Note, the primers can include a binding moiety, so any resultant amplicons can be captured at later process steps.

The location of the PCR forward and/or reverse primers is optimized to provide for maximal clamping of wild-type sequence. This is achieved by locating either primer close to or even within the sequence region complementary to the PNA clamp probe. Preferably one of the primers 3' terminal nucleic acid bases contains a portion of the PNA annealing sequence for maximal inhibition of PCR amplification of the wild-type sequence.

Unlike real time PCR methods, the present methods do not require extraction of nucleic acids from crude samples, e.g., in order to ensure sensitivity, reduced background, and to avoid false positive signals. For example, a common Real Time PCR (RTPCR) technique, a DNA-binding dye binds to all double-stranded (ds) DNA in the sample and PCR reaction, causing fluorescence of the dye. An increase in DNA product during PCR leads to an increase in fluorescence intensity and is measured at each cycle, thus allowing DNA concentrations to be quantified. However, dsDNA dyes such as SYBR Green™ will bind to all dsDNA and PCR products, including nonspecific PCR products (such as Primer dimer). This can potentially interfere with, or prevent, accurate quantification of the intended target sequence. Because the PCR product in the present methods do not provide a signal for stray nucleic acids in the sample, the above problems are avoided. Because detection is specific to labeled amplicons, and other PCR reaction constitutes are washed away before detection, samples in the present methods can be relatively crude, e.g., unextracted lysates, DNAzol™ lysates, PPFE slide scrapings, cells, biopsy tissues, needle biopsies, and the like.

Peptide nucleic acids (PNAs) do not have the phosphate backbone of natural nucleic acids. Without a negative charge in the backbone, PNAs are less repulsed than a natural nucleic acid from target nucleic acids. Thus, PNAs tend to bind stronger to their target complement. Another feature or PNAs is that they are more sensitive to base mismatches that natural nucleic acids. Further, PNAs are not substrates for DNA polymerases. This combination of characteristics means that PNA probes can stubbornly block (clamp) polymerase replication of a nucleic acid at a fully complementary sequence. On the other hand, the same PNA clamping probe can be configured to not block replication if there is even a single base mismatch in the sequence of interest, thus allowing creation of PCR amplicons where there is not full complementarity with the PNA clamping probe. The ability of PNA clamping/PCR to sensitively and specifically detect single base mutations, e.g., in a sample containing abundant wild type sequences can be valuable in detecting uncommon cells, such as cancer cells, among predominant normal cells, is a great improvement over prior technologies. The PCR primers are typically designed are using sequence walking flanking on both sides of the mutations.

The PNA clamping probe can be synthesized (e.g., on a solid support) from a PNA monomer protected with a benzothiazolesulfonyl (Bts), e.g., according to International Publication No. WO 03/091231, or from a PNA monomer protected with a 9-fluorenylmethloxycarbonyl (Fmoc) or r-butoxycarbonyl (t-Boc) group. Also see, e.g., Thomson et al., Tetrahedron 51(22): 6179-6194, 1995; Christensen J. Peptide Sci. 1(3): 175-183, 1995; and Dueholm et al., J. Org. Chem. 59(19): 5767-5773, 1994. The PNA clamping probes of the present methods are typically not labeled, e.g., with a reporter.

In a typical arrangement, the PCR primer probe sequences are selected to bracket a sequence of interest (as known in the art) so the sequence will be amplified unless it is blocked by a clamping probe. For example, if there is interest in detecting a sequence variant (e.g., a mutation) in a particular gene, a 5' PCR probe can be provided with a sequence hybridizing 5' to a sequence of interest on the coding strand, and a 3' PCR probe can be provided with a sequence hybridizing to the second strand of the target nucleic acid 3' from the sequence of interest. The PCR probes can be selected to bracket the PNA target sequence of interest. The hybridization temperatures of the primer probes typically range within 1, 2, 3, 4, or 5° C. of the PNA probe melting temperature, e.g., 75° C.+/−5° C. In the PCR reaction, the PCR primers are typically configured to have an annealing temperature at least 5° C. lower than the corresponding PNA clamping probe Tm. Most preferably the melting temperatures of the PNA clamping probe should be in excess of 70° C.

A PNA clamping probe can be designed to function with the primer probes to allow PCR amplification only where the sequence of interest has no sequence variants (e.g., a point mutation or more). For example, the PCR primers can be designed to have a melting temperature (Tm) of 65° C., while the PNA clamping probe can be designed to have a melting temperature of 70° C. hybridized to the wild type target sequence (while the Tm with a single base mismatch is, e.g., less than 50° C.). In this way, PCR amplification will be blocked for wild type sequences, but clamping probe will not hybridize and amplification will not be blocked for target sequences having a single base sequence variation.

At least one of the PCR primer probes used in the present methods will have a binding moiety, e.g., so that amplicons extended from the primer can be captured on a solid support. The binding moiety can be of any type having sufficient affinity and specificity to selectively capture the amplicon at the solid support. The binding moiety can be a member of a ligand/receptor pair, an antigen/antibody pair, hybridizing nucleic acid strand pair, metal/chelator pair, and/or the like. For example, the binding moiety on at least one PCR primer can be biotin, avidin, streptavidin, a hapten, a ligand, a receptor, a chelator, an antibody, digoxigenin, a polynucleotide comprising a sequence complementary to a capture probe, and a polynucleotide comprising a sequence complementary to a bDNA detection probe, or the like.

Optionally, at least one of the PCR primer probes used in the present methods will have a reporter binding moiety specific for a binding target providing a detectable signal. In this way, a reporter group can be associated with the amplicon, for detection on the solid support. The reporter binding moiety can be of any type having sufficient affinity and specificity to ultimately provide a confident signal above background at the detection step. The binding moiety can be a member of a ligand/receptor pair, an antigen/antibody pair, hybridizing nucleic acid strand pair, metal/chelator pair, and/or the like. For example, the binding moiety on at least one PCR primer can be biotin, avidin, streptavidin, a hapten, an antibody, digoxigenin, a polynucleotide comprising a sequence complementary to a capture probe, and a polynucleotide comprising a sequence complementary to a bDNA detection probe, or the like.

An unexpected benefit of the present methods is the surprise result that excess primer probe does not significantly interfere with the detection step. Where the primer includes a reporter or a reporter-binding moiety, no background signals are developed because these primers are not bound to the solid support and are washed away from the solid support capture surface before the detection step. Further, although remaining unincorporated primer with binding moiety can theoretically bind and compete for capture sites on the capture solid support, this has not been a problem. Amplification reactions with standard primer concentrations do not interfere with capture and detection of product amplicons. We have found it unnecessary to address unincorporated binder capture competition, e.g., by adjusting stoichiometry (binding moiety primer molarity) or by separation of excess primer from amplicons, although these concepts are newly disclosed herein. For example, although signal may be increased by minimizing the PCR reaction molarity, running the reaction to primer exhaustion, or separation of primers (e.g., by size exclusion), such additional steps are surprisingly unnecessary in many embodiments. For example, PCR products can be detected and quantitated starting from PCR cycles where they would not yet be detected in a real time PCR assay.

Alternately, in certain embodiments, at least one primer can include a reporter detectable without the requirement to capture or bind a label system or external label from solution before or after capture at the solid support. For example, at least one of the primer probes (and ultimate amplicon) can be directly labeled with a reporter, such as an enzyme, fluorophore, radionuclide, or gold particle. Optionally, the amplicons can include a reporter binding moiety to capture a label at any appropriate step of the method.

The amplicons of the method can be specifically captured on a solid support. Depending on the binding moiety chosen for attachment to a primer probe, the other appropriate binding pair member can be provided on the surface of the solid support to capture the amplicon extended from the probe when the PCR reaction mixture contacts the solid support. For example, where the primer probe binding moiety is a hapten, the solid support can have a surface populated with antibodies specific to that hapten. Optionally, where the binding moiety is biotin, the solid support can be populated with an avidin peptide. Alternately, the primer probe can have a poly-his tag and the solid support can display a nickel ion, or other appropriate metal. In a preferred embodiment, the primer probe has a capture target sequence (e.g., as a 5' tag) that can hybridize with a complementary nucleic acid (DNA, RNA, PNA) capture probe on the solid support.

Solid Support Capture and Detection

The product of a PNA clamped PCR reaction may include amplicons, e.g., when sequence variants are present in the target region of the PNA clamping probe. Because at least one of the PCR primers includes a binding moiety, the amplicon from extension of the primer will include the binding moiety. Further, at least one of the primers can include a reporter or reporter binding moiety so the presence of any amplicon can be detected directly or indirectly.

Figure 2:
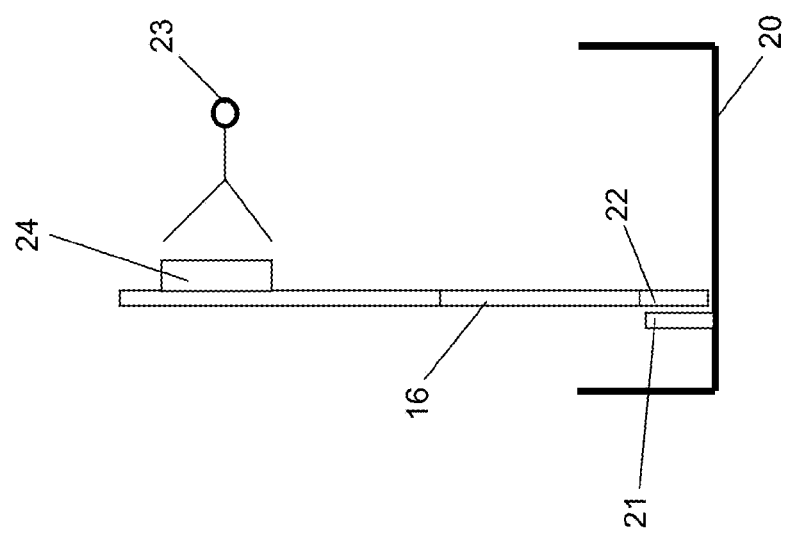
FIG. 2 is a schematic diagram showing solid support capture of amplicons.

In the detection stage of the methods, a solid support 20 presenting a specific affinity capture moiety 21 is contacted with the PNA clamp/PCR reaction solution, as shown in FIG. 2. If an amplicon 16 product is present (because a target variant prevented clamping by the PNA probe) it will have a binding moiety 22 with an affinity for the capture moiety on the solid support. Contact between the amplicon and solid support will result in capture of the amplicon on the solid support. At this point, excess PCR reaction constituents can be washed away, thus greatly reducing non-specific background noise.

In certain embodiments, at this point in the method, a detector system 23 can contact the solid support environment and determine whether there is captured amplicon present or not. For example, if the PCR employed a first primer with a binding moiety directed to a solid support capture moiety, and a second primer with a reporter group (such as a fluorescein), the resultant amplicon would be captured on the solid support and directly detectable, e.g., by interrogation with a fluorometer.

In some embodiments, captured amplicons are detectable after binding of a reporter group 23 to a reporter-binding moiety 24, e.g., introduced to the amplicon as part of the second PCR primer. If the PCR employed a first primer with a binding moiety directed to a solid support capture moiety, and a second primer with a reporter-binding moiety (such as a biotin), the resultant amplicon could be detected after binding of the reporter to the reporter-binding moiety. For example, amplicon could be captured on the solid support, the support washed, and the surface contacted with the reporter. Any reporter not bound to captured amplicon could be washed away. Assuming the reporter-binding moiety were biotin and the reporter were avidin-fluorescein, the surface could be scanned with a fluorometer to detect any amplicon. Alternately, during the method, the reporter could be bound to the reporter-binding moiety before or during capture of the amplicon on the solid support.

In still other embodiments, the detection can take additional development steps. For example, the reporter-binding moiety can be a hapten and the reporter an antibody/enzyme. The captured amplicon can be contacted with the reporter and washed, thus locating enzyme at the solid support location. Assuming the enzyme (e.g., alkaline phosphatase or horseradish peroxidase) has a colorimetric substrate, a visible color could be developed at the solid support location by application of the substrate. Such a signal could be detected by a technician and/or by electronic detector.

Figure 3:
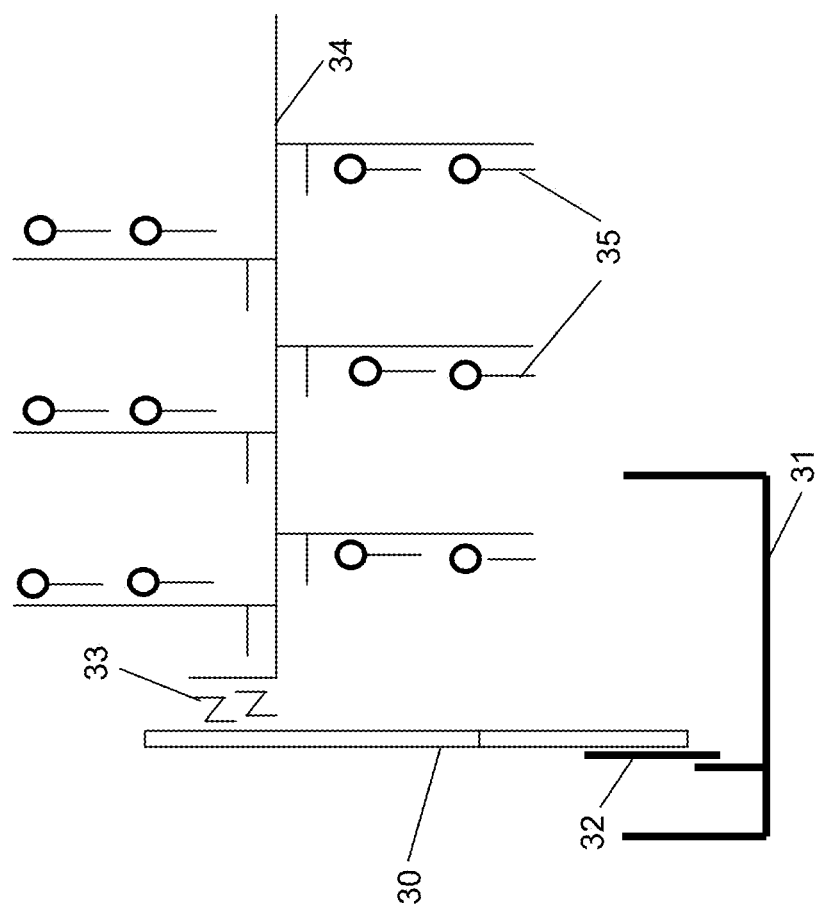
FIG. 3 is a schematic diagram of a bDNA detection technique.

In a preferred embodiment, the detection system comprises elements of a bDNA assay. For example, at the PNA clamping/PCR stage, one or more of the PCR primers can include a nucleic acid sequence configured to hybridize with elements of a bDNA capture system on a solid support. Briefly, bDNA assays specifically capture nucleic acids of interest and provide an amplified signal of their presence. In a typical case of bDNA amplification, shown in FIG. 3, a target nucleic acid 30 (e.g., an amplicon) is captured on a solid support 31 by a capture extender 32. The captured target is decorated at one or more specific sequence locations with label extenders 33. The label extenders are commonly associated with branched DNA molecules 34 capable of binding multitude label probes 35 to generate a large signal associated with the initial capture of a small amount of target. The label probes can be oligonucleotides bound to a fluorescein, or other reporter readily detected, as known in the art.

More specifically, the method of detection of the present invention can be carried out using the principles set forth in the QuantiGene™ method described in U.S. Pat. No. 7,709, 198, and is incorporated herein by reference. The QuantiGene™ method uses a branched DNA technology in a series of hybridization reactions without the need for thermal cycling for amplification of a signal. In principle, it uses a set of primary probes to hybridize to a target sequence and the presence of such hybridization is intensified via additional probes hybridizing to part of these primary probes, as described above. Thus, the base identity of a point mutation variant can be determined.

The methods above can be practiced as matrix or array configured assays. For example, if a mutation of interest is at a particular position, the PNA clamping/PCR reaction could be carried out in four different reaction wells, each including a PNA probe with a different base at that position. Only base mismatches at that position would ultimately provide a signal, reactions with no signal have the base complement at the position. Thus, the mutation is sequenced.

In another example, multiple sets of primers/clamp probes are added to a sample; each set directed to a different target sequence. In addition, each set includes a primer with different reporter signal or reporter-binding moiety. Depending on the signal ultimately generated (e.g., different fluorescent colors) the information can be interpreted to confirm the presence of one or more variants in the same sample, e.g., at different positions along the nucleic acid, or on different nucleic acids of the sample.

In another example, multiple sets of primers/clamp probes are added to a sample; and each set directed to a different target sequence. In addition, each set includes a primer with different binding moiety, e.g., specific to different solid support capture moieties. In this example, the solid support can include more than one region (e.g., an array or series of different beads) with different capture moieties. Depending on the region(s) where signal(s) are ultimately detected, one can determine which probe set(s) were directed to a target sequence having a mismatch with each particular clamp probe. That is, one can see on an array format whether any two or more specific targets in the single sample had a sequence variant.

In any of the above methods (e.g., single assays, multiple assays, matrixed assays, and arrays), the amount of a sequence variant can be quantitated. An advantage of the present methods, not found in the prior art, is that the PCR step can be stopped at a stage wherein maximum linear amplification is achieved, but not necessarily at the stage of maximum amplicon accumulation. PCR can be stopped at a stage wherein the quantity of amplicons is most quantitative, or even at a cycle before amplicon would have been detected in standard RT PCR. That is, e.g., the amount of amplicon at about 15 cycles is more closely proportional to the initial number of target sequences than it is at 40 cycles. Because, e.g., bDNA methods can provide a strongly amplified and proportionate signal, detection of a PCR pre-amplified target can be extremely sensitive, precise, and accurate over a broader range than for PCR alone.

Systems for Detecting Sequence Variants

Figure 4:
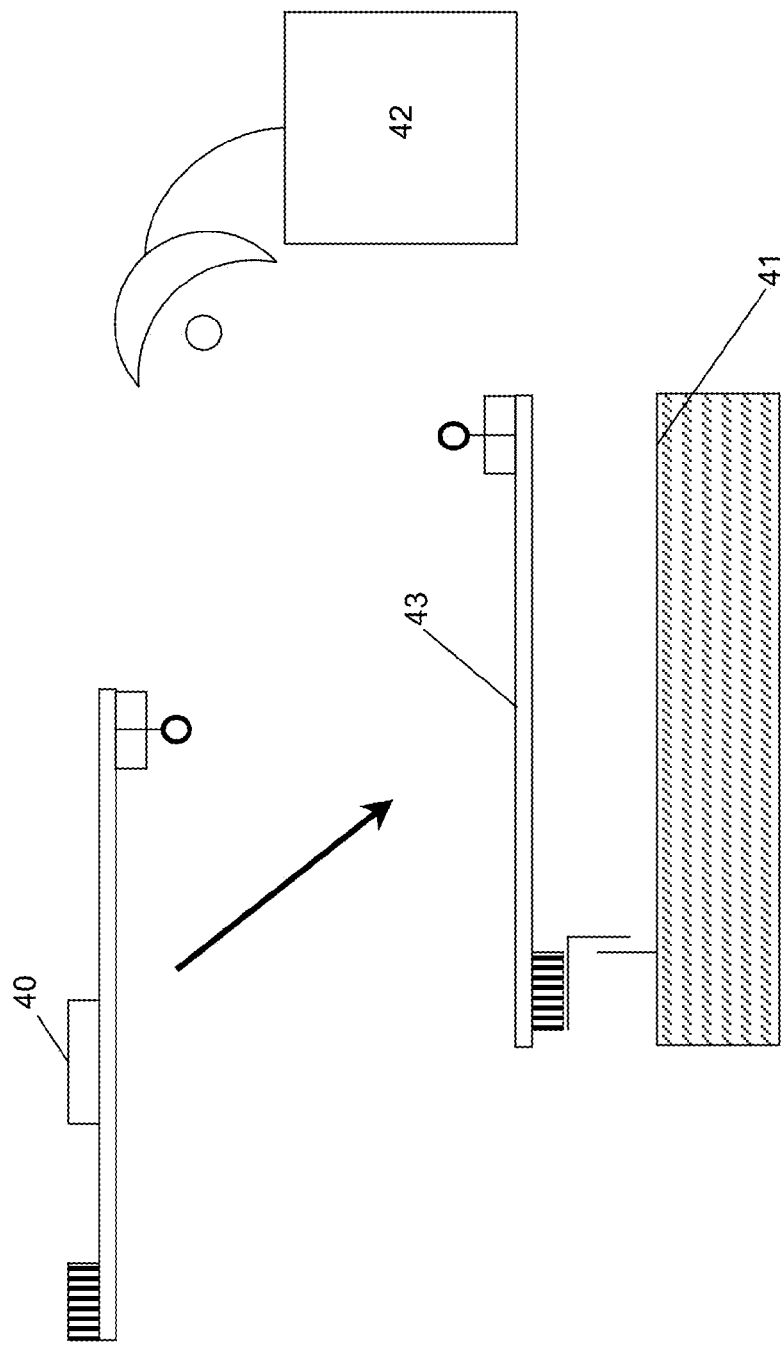
FIG. 4 is a schematic diagram of an exemplary system for detection of sequence variants.

Systems for detecting and quantitating sequence variations include components for initial amplification of variant targets, and components for solid support detection of the amplified product. In general, the inventive systems include PCR reagents and hardware, one or more PNA clamping probes 40 directed to a sequence of interest, a solid support affinity capture surface 41, and a detector 42 adapted to detect the presence of PCR amplification product (amplicons 43) captured on the solid support surface, as shown in FIG. 4.

The PCR primer probes are typically DNA oligomers ranging in length from about 8 bases to 40 bases, 10 bases to 30 bases, 15 bases to 25 bases, or about 20 bases. The probe sequences can be adjusted, e.g., by probe length and sequence, to have a melting temperature (Tm) of about 70° C. or more with target in the PCR buffer. The probes can be adjusted so that the 5' and 3' probes have similar melting temperatures. Typically, under PCR conditions, the primer probes have a Tm less than that of the PNA clamping probe.

A key aspect of the systems for detection of sequence variants is that at least one of the PCR primers includes a binding moiety, e.g., with specific affinity for an intended binding a capture moiety on the solid support. As the primers are extended by the polymerase in the PCR amplification, the primers with their binding moieties are incorporated into the amplicons. Thus, the amplicons can be bound to the solid support, allowing other PCR reaction components to be washed away. With background noise substantially reduced, the sensitivity and linearity of detections is greatly increased.

The binding moiety on a primer probe can be any appropriate to the intended solid support capture. For example, the binding moieties (as discussed above in the Methods section) can be an affinity pair member, e.g., antibody or antigen, a member of a pair of hybridizing nucleic acid sequences, ligand or receptor, chelator or a metal, and/or the like. For example, the binding moiety can be biotin, avidin, streptavidin, a hapten, an antibody, a fluorescein, digoxigenin, a polynucleotide comprising a sequence complementary to a capture probe, and a polynucleotide comprising a sequence complementary to a bDNA detection probe, or the like.

One or more of the PCR primer probes can also include a detectable reporter or reporter binding moiety. For example, the primer can have a directly detectable group, such as a fluorescent group, enzyme, radionuclide, chromophore, gold bead, etc. Optionally, the primer can have an affinity group capable of specifically binding to a detectable group. The reporter binding group (moiety) can be designed to bind to a target on a desired reporter group. For example, the reporter binding moiety can be a hapten and the reporter an enzyme linked to an antibody to the hapten. The reporter binding moiety can be biotin and the reporter a fluorophore linked to an avidin molecule. Typically, the reporter binding moiety binds to a different affinity partner than the capture binding moiety.

PNA clamping probes have peptide bonds in the backbone chain instead of the phosphate found in DNA. Typically, the PNA probes have natural base groups (A, T, G, C, U), as found in natural nucleic acids. However, unnatural bases can be used, e.g., if they provide adequate hybridization stringency and specificity. Because PNAs typically have a stronger binding affinity than natural nucleic acids, PNA probes are often the same length or shorter than partnered PCR primer probes. The PNA clamping probes typically DNA range in length from about 5 bases to 30 bases, 7 bases to 25 bases, 10 bases to 20 bases, or about 17 bases. The probe sequences can be adjusted, e.g., by probe length and sequence, to have a melting temperature (Tm) between about 70-86° C. (or about 75° C.) with target in the PCR buffer. PNA probes are typically present at a concentration of about 0.1 um in the reaction. Typically, under PCR conditions, the PNA clamping probes have a Tm higher than that of the primer probes. Typically, the PNA clamping probes are not labeled, e.g., with a binding moiety, a reporter group, or reporter binding moiety.

The products of a PNA clamping/PCR reaction, according to the methods described above, can be selectively harvested on a solid support for detection. Exemplary solid supports include beads, semiconductor wafers, multiwell plates, planar arrays, and the like. The solid supports are typically insoluble in the solutions and fluids to which they are exposed in the methods.

In some embodiments of the invention, the solid support has a planar surface and is typically rigid. The planar surface can be, e.g., the surface of a slide or an interior surface of a compartment or well. Exemplary materials for the solid support include, but are not limited to, glass, silicon, silica, quartz, plastic, polystyrene, nylon, a metal, a ceramic, and nitrocellulose. The solid support can, e.g., be a multiwell plate or a glass slide with an array of capture probes laid out in a grid pattern at selected positions. The solid support can be configured as an electronic sensor, e.g., monitoring capacitance, resonance, or the like, e.g., in response to the amount of amplicons captured on the surface.

In embodiments involving assay of a large number of samples in parallel, or multiplexed embodiments wherein many target nucleic acids are assayed from the same sample at once, the nucleic acids (e.g., sample nucleic acids of interest or associated amplification oligomers) can be captured at different positions on a non-particulate, spatially addressable solid support. Thus, in one class of embodiments, the solid support comprises two or more capture moieties, each at different selected positions on the solid support.

In a certain multiplexed example, the solid supports are microspheres (e.g., small beads). The microspheres of each subset can be distinguishable from those of the other subsets, e.g., on the basis of their fluorescent emission spectrum, their diameter, bar code labels, or a combination thereof. For example, the microspheres of each subset can be labeled with a unique fluorescent dye or mixture of such dyes, quantum dots with distinguishable emission spectra, and/or the like.

Suitable instruments and software for analyzing captured amplicons can include any suitable for a particular reporter group and solid support format. For example, detectors can include fluorometers, 96-well plate readers, flow cytometers, charge coupled devices, photoarrays, and the like. In many formats, a technician can visually scan a solid support surface to detect and identify signals. Captured amplicons can also be visualized using gold particle labeled antibodies or other gold labeled binding moiety. Such detection of mutant amplicons could be performed in a simple strip based assay format.

EXAMPLES

The following examples are offered to illustrate, but not to limit the claimed invention.

Example 1

QClamp PCR PNA Clamping for Mutation Detection

It is understood that the examples and embodiments described herein are for illustrative purposes only and that various modifications or changes in light thereof will be suggested to persons skilled in the art and are to be included within the spirit and purview of this application and scope of the appended claims.

QClamp PCR is a method that uses a synthetic peptide nucleic acid (PNA) to bind to a region of a target gene sequence that spans a known mutation site or 'hot spot' in a target gene. Examples of such target genes include oncogenes, proto-oncogenes, tumor suppressors, growth factor receptors and tumor associated signal transduction protein kinases for example: K-Ras, B-Raf, EGFR, p53, PI3KCA, IDH1, JAK2, p53, PTEN, INK, pRb, ARF, mTOR, ALK, Akt, etc.

A region of the target gene containing known mutation(s) is selected and primers designed to amplify this region employing polymerase chain reaction (PCR). A peptide nucleic acid (PNA) is designed such that it binds selectively to the wild-type (non-mutant) sequence of the target gene. Because the binding of PNA to WT DNA is much stronger than to the single base pair mutant gene sequence because of the superb base discrimination capability of PNA. PNA does not act as a primer for Taq polymerase and essentially blocks or 'clamps' the wild type sequence such that a wild-type amplicon cannot be generated. Only mismatched gene sequences are amplified resulting in formation of an amplicon derived only from the mutant gene sequence.

PNA clamping has been used for many years to detect single base mutations in target genes in KRas, BRAF, EGFR, PI3KCA, etc. However, all of these reported techniques use fluorescent real-time PCR to detect the resulting mutant amplicon. In the present inventions, we use a capture format to detect the amplicon by using forward and reverse primers that contain a binding and/or recognition moiety (reporter or reporter binding moiety). Such moieties include molecules such as: biotin that are recognized and bound tightly and selectively by avidin or streptavidin; fluorescein that is recognized and bound tightly by anti-fluorescein antibodies; digoxigenin that is recognized and bound tightly by anti-digoxigenin antibodies; or oligonucleotide probe sequences that can be hybridized to complementary capture and/or detection probe sequences.

PCR primers bearing such covalently attached recognition moieties are used to amplify the target sequence of interest using PCR with a PNA probe that binds selectively to the wild-type gene sequence. After PCR amplification, the amplicon is captured by the complementary binding partner to the recognition moiety (e.g., streptavidin, antibody or complementary oligonucleotide sequence) immobilized on a solid-phase (e.g., beads, microparticles or microplate).

After incubation and washing, the bound amplicon is detected by addition of a reporter having an affinity for the amplicon reporter-binding moiety. The reporter can be, e.g., an enzyme, fluorophore, or gold particle. After washing, any bound reporter is detected by use of a luminescent, fluorescent, or colorimetric enzyme substrate, e.g., if the reporter group is an enzyme. Optionally, detection can be by fluorescence or optical detection, e.g., if the reporter group is a fluorophore or gold particle.

This provides a unique and novel way to detect mutant amplicons generated by a PNA clamping PCR reaction for the detection of mutant allele or somatic mutations in target genes particularly those associated with cancer, viral and bacterial diseases that have developed drug resistant mutations in target genes. The technology is applicable to the detection of all known mutations in any target gene of interest whether derived from mammalian, viral, bacterial, fungal, or plant origins.

Example 2

Preferred PNA Clamping/PCR Probe Configurations

We have seen surprising and dramatic differences in PCR clamping efficiency if we either increase the Tm of the PNA probe; by increasing the number of bases flanking the mutation sequence located at the center of the PNA clamp probe, or move the forward or reverse primer sequence close to or even partly overlapping the clamping sequence site. When discriminating mutations like the codon 12 and codon 13 in KRAS and NRAS it is necessary to do this to be able to discriminate which codon has the mutation.

To enhance selectivity and discrimination of the PNA clamping/PCR assays, it is preferred to locate the expected mutant base position in the PNA probe to a position near the center of the PNA probe sequence.

The number of bases on each side of the expected mutation base position of interest can be less than 5 bases, 6, 7, 8, 9, 10, 11 or more. In many typical embodiments it is preferred to have about 8 bases on each side of the expected mutant base position. In instances where discrimination is particularly difficult (e.g., where similar bases or interest are in similar positions), it can be preferred to configure the PNA probe with more than 8 bases on each side of the expected mutant base position.

In many cases, the discrimination of the presence or absence of a mismatch to the PNA clamping probe can surprisingly enhanced substantially by configuring the PCR primer probes to hybridize at positions close to the PNA probe target footprint, or even overlapping the footprint somewhat. For example, the ability to distinguish no mismatch from a single mismatch can be increased by locating one or more PCR primer within 10 bases, 8 bases, 6 bases, 4 bases, or 2 bases from the PNA clamping probe target. Further, significant improvements in discrimination can be provided wherein one or both PCR primer probes are configured to be adjacent to the PNA probe, or overlap the PNA probe by 1, 2, or more bases.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting a variant in a target nucleic acid of interest, the method comprising:
    providing a first pair of PCR primer probes which allow formation of a PCR process product comprising a sequence covering a first region of interest in the target nucleic acid, wherein at least one of the primer probes comprises a binding moiety;
    providing a first PNA clamping probe fully complementary to a clamping target sequence in the nucleic acid target region of interest;
    admixing the primer probes and clamping probe with a putative target nucleic acid sample;
    performing a PCR amplification process in a reaction solution under hybridization conditions wherein the clamping probe hybridizes to a perfect complement clamping target sequence, but does not hybridize where there are one or more sequence variants in the clamping target sequence, thereby producing PCR amplicons comprising one or more primer probes only if the clamping target sequence includes one or more a sequence variants;

providing one or more capture moieties on a solid support, which capture moieties are adapted to bind the binding moiety;

contacting the solid support with the PCR reaction solution, thereby capturing PCR amplicons present in the solution; and, interrogating the solid support to determine the presence or absence of bound amplicons on the solid support;

whereby the presence of a variant in the target sequence of interest is confirmed by detection of amplicons on the solid support; and wherein the presence of the amplicons is detected using a bDNA assay.

2. The method of claim 1, wherein the binding moiety or capture moiety is selected from the group consisting of: biotin, avidin, streptavidin, a hapten, an antibody, fluorescein, digoxigenin, a ligand, a receptor, a polynucleotide comprising a sequence complementary to a capture probe, and a polynucleotide comprising a sequence complementary to a bDNA detection probe.

3. The method of claim 1, wherein the nucleic acid target region of interest consists of a sequence selected from the group consisting of: an oncogene, a proto-oncogene, a tumor suppressor, a growth factor receptor, a tumor associated signal transduction protein kinase sequence, a K-Ras sequence, a B-Raf sequence, an EGFR sequence, a p53 sequence, a PI3KCA sequence, an IDH1 sequence, a JAK2 sequence, a PTEN sequence, an INK sequence, a pRb sequence, an ARF sequence, a mTOR sequence, an ALK sequence, and an Akt sequence, or a natural mutant thereof.

4. The method of claim 1, wherein the clamping target sequence in the nucleic acid target region comprises a sequence ranging from 12 bases to 25 bases.

5. The method of claim 1, wherein the sequence variant comprises a single base pair mismatch between the PNA probe and the target.

6. The method of claim 1, wherein the sample is a cell lysate not extracted to separate nucleic acids from other lysate constituents before said admixture.

7. The method of claim 1, wherein the sample comprises nucleic acids extracted from cell, nucleic acids extracted from tissue, purified nucleic acids, or synthetic nucleic acids.

8. The method of claim 1, wherein solid support is selected from the group consisting of: beads, microparticles, a multiwell plate, a semiconductor, and a microplate.

9. The method of claim 1, further comprising providing a second pair of PCR primer probes which allow formation of a PCR process product comprising a sequence covering a second region of interest in the target nucleic acid; and providing a second PNA clamping probe fully complementary to a second clamping target sequence;

whereby both the first and second clamping target sequences can be evaluated for the presence of variants in the same sample.

10. A system for detecting a variant in a target nucleic acid of interest, the system comprising:

a) PCR amplification process reaction solution comprising:

a pair of PCR primer probes which allow formation of a PCR process product comprising a sequence covering a region of interest in the target nucleic acid, wherein at least one of the primer probes comprises a binding moiety; and, a PNA clamping probe fully complementary to a clamping target sequence in the nucleic acid target region of interest;

b) a solid support comprising a surface with one or more capture moieties adapted to bind the binding moiety; and, c) a detector adapted to detect one or more of the pair of primer probes on the solid support; and d) a bDNA detection system comprising, label extenders, amplification multimers or label probes.

11. The system of claim 10, wherein one or more of the primer probes comprise a binding target with an affinity for a label system.

12. The system of claim 10, wherein the clamping probe is adapted to have a melting temperature less than the primer probe melting temperatures when the clamping target has a sequence variant.

13. The system of claim 10, wherein the solid support is selected from the group consisting of: beads, microparticles, a semiconductor, and a microplate.

14. The system of claim 10, wherein the one or more capture moieties are biotin groups, bDNA capture probes, or capture extenders.

15. The system of claim 10, wherein a first of the primer pair comprises a biotin, and a second of the primer pair comprises a fluorescein or a digoxigenin.

16. The system of claim 10, wherein, further comprising a second pair of PCR primer probes different from the first pair, and a second PNA clamping probe fully complementary to a second clamping target sequence.

* * * * *